United States Patent
Nord et al.

(10) Patent No.: US 11,759,655 B2
(45) Date of Patent: Sep. 19, 2023

(54) METHOD AND APPARATUS FOR USING A MULTI-LAYER MULTI-LEAF COLLIMATION SYSTEM

(71) Applicant: Varian Medical Systems International AG, Cham (CH)

(72) Inventors: Janne I. Nord, Espoo (FI); Esa Kuusela, Espoo (FI); Jarkko Y. Peltola, Tuusula (FI); Juha Kauppinen, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 0 days.

(21) Appl. No.: 15/794,198

(22) Filed: Oct. 26, 2017

(65) Prior Publication Data
US 2019/0126069 A1    May 2, 2019

(51) Int. Cl.
*A61N 5/10* (2006.01)
*G21K 1/04* (2006.01)

(52) U.S. Cl.
CPC ......... *A61N 5/1045* (2013.01); *A61N 5/1047* (2013.01); *G21K 1/046* (2013.01); *A61N 5/1036* (2013.01)

(58) Field of Classification Search
CPC .. A61N 5/1045; A61N 5/1036; A61N 5/1047; G21K 1/046
USPC ...................................................... 250/505.1
See application file for complete search history.

(56) References Cited

U.S. PATENT DOCUMENTS

| | | | | |
|---|---|---|---|---|
| 4,868,844 | A * | 9/1989 | Nunan | G21K 1/046 378/204 |
| 8,519,370 | B2 * | 8/2013 | Luzzara | A61N 5/1045 250/505.1 |
| 10,987,523 | B2 * | 4/2021 | Sheng | A61N 5/1036 |
| 2001/0043669 | A1 | 11/2001 | Ein-Gal | |
| 2012/0256103 | A1 | 10/2012 | Luzzara | |
| 2014/0112453 | A1 * | 4/2014 | Prince | G21K 1/046 378/152 |

FOREIGN PATENT DOCUMENTS

| | | |
|---|---|---|
| CN | 105727449 A | 7/2016 |
| CN | 106552324 A | 4/2017 |
| EP | 0256989 A1 | 2/1988 |
| EP | 0314231 A2 | 5/1989 |

(Continued)

OTHER PUBLICATIONS

Wijesooriya; et. al, "Determination of maximum leaf velocity and acceleration of a dynamic multileaf collimator: Implications for 4D radiotherapy", Med. Phys. 32 (4), Apr. 2005, pp. 932-941 (Year: 2005).*

(Continued)

*Primary Examiner* — David A Vanore
(74) *Attorney, Agent, or Firm* — Fitch, Even, Tabin & Flannery LLP

(57) ABSTRACT

A multi-layer multi-leaf collimation system includes at least a two layers of collimation leaves. The first multi-leaf collimator layer is configured to primarily perform a first function to affect a radiation beam traveling from a radiation source to a target and a second multi-leaf collimator layer is configured to primarily perform a second function, different from the first function, to affect the radiation beam for the administration of a treatment plan.

6 Claims, 3 Drawing Sheets

(56) References Cited

FOREIGN PATENT DOCUMENTS

EP          3146998  A1    3/2017
WO      2012027180  A2    3/2012
WO      2017070433  A1    4/2017

OTHER PUBLICATIONS

PCT Search Report and Written Opinion from International Application No. PCT/EP2018/077929, dated Jan. 23, 2019; 16 pages.
Chinese First Office Action from related Chinese Patent Application No. 201880068406.X dated Dec. 3, 2021, English translation included; 20 pages.
Chinese Second Office Action from related Chinese Patent Application No. 201880068406.X dated Jul. 13, 2022, English translation included; 16 pages.
Rejection Decision from related Chinese Patent Application No. 201880068406.X dated Jan. 5, 2023, 7 pages. No English translation or summary is currently available.
Article 94(3) EPC from related European Patent Application No. 18786325.3 dated Jan. 5, 2023, 4 pages.

* cited by examiner

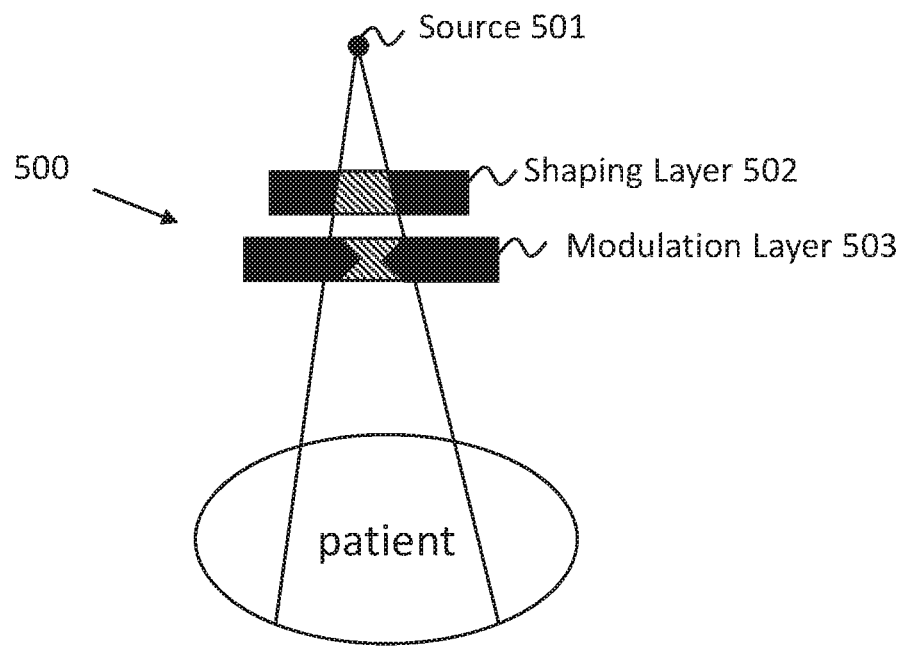
*FIG. 5*
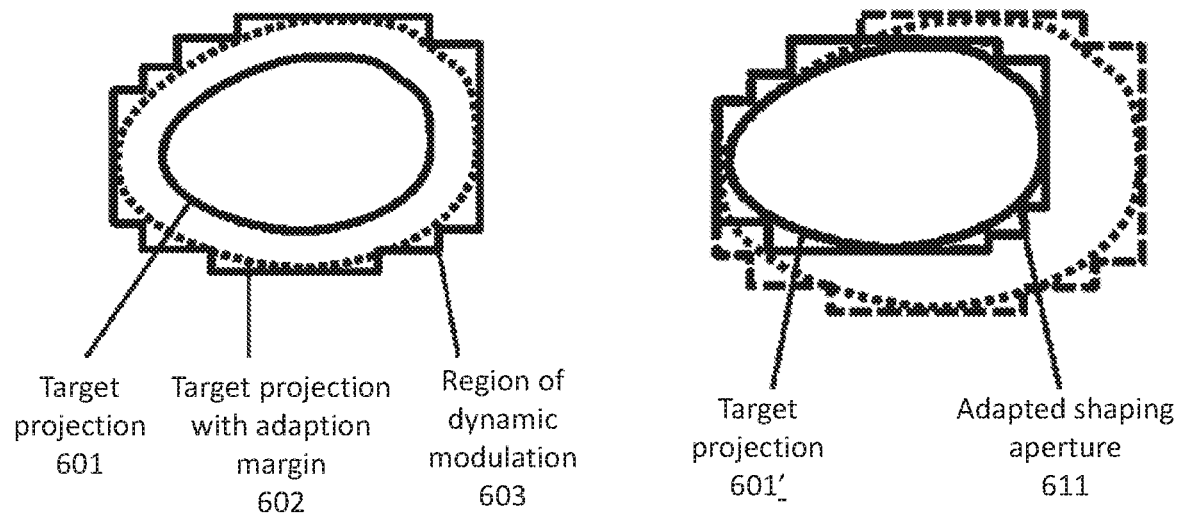
*FIG. 6A*            *FIG. 6B*

METHOD AND APPARATUS FOR USING A MULTI-LAYER MULTI-LEAF COLLIMATION SYSTEM

TECHNICAL FIELD

These teachings relate generally to the administration of therapeutic doses of radiation and more particularly to the use of multi-leaf collimators.

BACKGROUND

Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and that can selectively move towards and away from one another via controlled motors. A typical multi-leaf collimator has many such pairs of leaves, often upwards of twenty, fifty, or even one hundred such pairs. A multi-layer multi-leaf collimator refers to a multi-leaf collimator with two or more layers of leaves positioned generally perpendicularly along the beam path of the radiation.

By passing a therapeutic radiation beam through the aperture(s) of a multi-leaf collimator, the radiation beam can be modulated to better match the dosing requirements of the treatment session. These dosing requirements typically include (or at least presume) prescribing which body tissues to irradiate and which body tissues to avoid irradiating.

Common methods of delivering modulated fields for radiation treatment include moving multi-leaf collimator leaves while the beam is on and other axes of the treatment delivery system are in motion. The achievable speeds of various components of the system constrains the treatment plan that can be administered by the system. In conventional multi-layer multi-leaf collimator designs, layers of leaves are typically set close to each other to reduce obstruction and generally have uniform motion capabilities. As such, the motions of collimator leaf layers do not deviate from each other substantially for treatment planning and treatment administration.

While a typical multi-layer multi-leaf collimator presents many benefits, the uniform motion capabilities of conventional collimator leaf layers are a significant constraint on the optimization and utilization of the multi-layer multi-leaf collimator and limit the system's treatment administration efficiency.

BRIEF DESCRIPTION OF THE DRAWINGS

The above needs are at least partially met through provision of the method and apparatus for using a multi-layer multi-leaf collimation system described in the following detailed description, particularly when studied in conjunction with the drawings, wherein:

FIG. 5 comprises an illustration of a collimator system in accordance with various embodiments of these teachings; and FIGS. 6A and 6B comprise illustrations of projections in accordance with various embodiments of these teachings.

Figure 1:
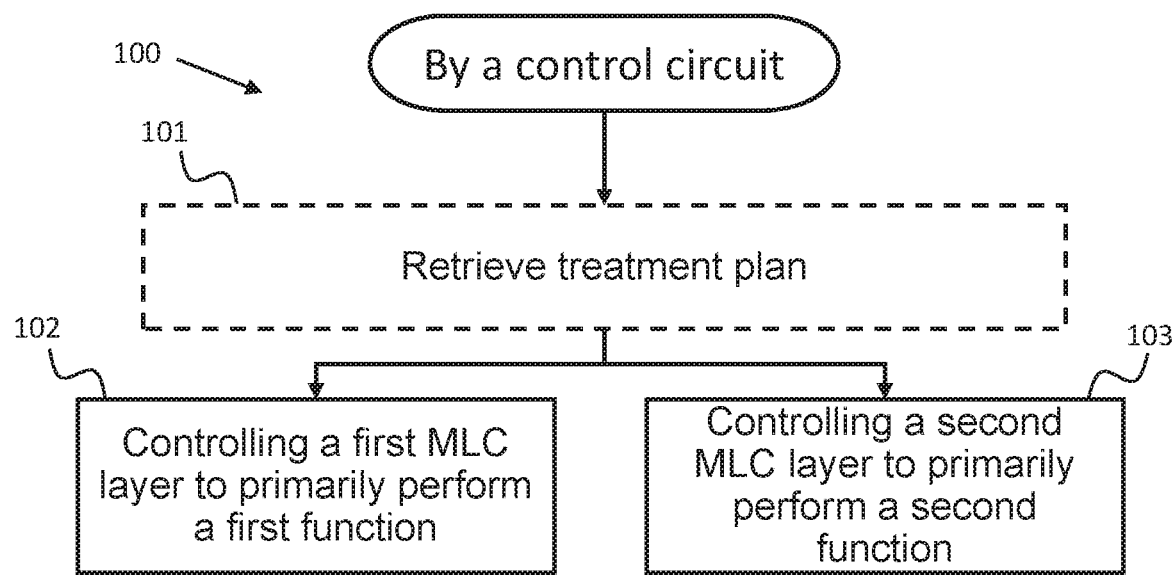
FIG. 1 comprises a flow diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an apparatus for radiation modulation in radiation therapy includes a first multi-leaf collimator layer configured to primarily perform a first function to affect a radiation beam traveling from a radiation source to a target. The apparatus further includes a second multi-leaf collimator layer configured to primarily perform a second function, different from the first function, to affect the radiation beam. The resultant radiation beam can then be used to administer radiation to a patient according to a treatment plan. (As used herein, this reference to being "configured" to primarily perform a particular function refers to more than merely using a given layer to effect a particular function. Instead, this reference will be understood to mean that the layer itself is specifically physically structured to effect the corresponding function.)

By one approach, in the apparatus for radiation modulation, the first function performed by the first multi-leaf collimator layer is shaping the radiation beam. For example, the radiation beam may be shaped by forming a first aperture according to a profile of a target area of a treatment plan to block out radiation outside of the target area. Accordingly, per this approach, the first function is to mask areas (such as organs that are near a tumor that is the target of the treatment) that are to be protected from the radiation, By one approach, in the apparatus for radiation modulation, the second function performed by the second multi-leaf collimator layer is modulating a fluence distribution of the radiation beam (for example, within the intended treatment volume). For example, fluence distribution may be modulated by modulating a second aperture to vary radiation intensities in different regions within a target area according to a treatment plan.

By one approach, in the apparatus for radiation modulation, the first multi-leaf collimator layer substantially differs from the second multi-leaf collimator layer in one or more of leaf transmission, penumbra width, maximum leaf speed, and median leaf width. For example, the first multi-leaf collimator layer may have leaves with widths between 2 mm and 2 cm and the second multi-leaf collimator layer may have leaves with widths between 5 mm and 5 cm.

In lieu of the foregoing or in combination therewith, an apparatus for radiation modulation in intensity modulated radiation treatment includes a first multi-leaf collimator layer having a first set of leaves configured to affect a radiation beam traveling from a radiation source to a target and a second multi-leaf collimator layer having a second set of leaves configured to affect the radiation beam along with the first multi-leaf collimator layer. By one approach the median width of the second set of leaves is substantially larger than the median width of the first set of leaves. The first multi-leaf collimator layer and the second multi-leaf collimator layer may be configured to primarily perform different functions.

In lieu of the foregoing or in combination therewith, a method for radiation modulation in radiation therapy includes the steps of controlling a first multi-leaf collimator layer being an integral part of a discrete multi-leaf collimator to primarily perform a first function to affect a radiation beam traveling from a radiation source to a target, and controlling a second multi-leaf collimator layer also being an integral part of the discrete multi-leaf collimator to primarily perform a second function, different from the first function, to affect the radiation beam.

So configured, in one or more of these approaches, the movements of different layers of a multi-layer multi-leaf-collimator are optimized for different functions to collectively administer a treatment plan. The leaves in each layer may be optimized according to that layer's specific maximum speed constraint for layer-specific functions. For example, a layer with a lower maximum speed may be used primarily for conformal apertures and a faster layer may be used to produce fast modulation. By some approaches, a multi-layer multi-leaf collimator may be used for adaptive treatment delivery by using the first layer to modulate the beam intensity profile to a region somewhat larger than the expected target projection and using the second layer to restrict the aperture to the target projection at the time of the treatment. These approaches generally improve upon conventional processes by increasing the optimization and operational efficiency of a multi-layer multi-leaf collimator.

Figure 2:
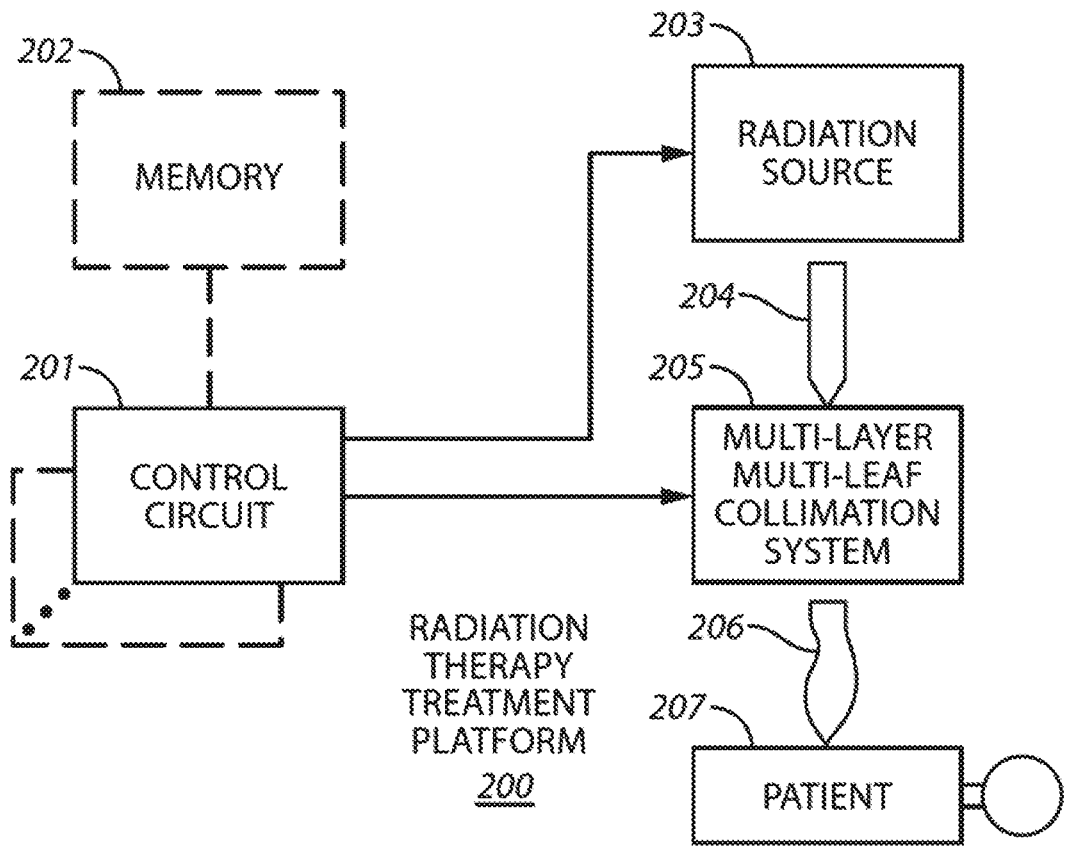
FIG. 2 comprises a block diagram as configured in accordance with various embodiments of these teachings.

These and other benefits may become clearer upon making a thorough review and study of the following detailed description. Referring now to the drawings, and in particular to FIG. 1, an illustrative process 100 that is compatible with many of these teachings is presented below. For the sake of an illustrative example, it is presumed herein that a control circuit of choice carries out the steps, actions, and/or functionality of this process 100. FIG. 2 presents an illustrative example in this regard.

As shown in FIG. 2, a radiation therapy treatment platform 200 can include or otherwise operably couple to a control circuit 201. Being a "circuit," the control circuit 201 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 201 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 201 is configured (for example, by using corresponding programming as will be well understood by those skilled in the art) to carry out one or more of the steps, actions, and/or functions described herein. It will also be understood that a "control circuit" can comprise multiple such components or platforms as well as suggested by the phantom control circuit box in FIG. 2.

By one optional approach the control circuit 201 operably couples to a memory 202. This memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

In addition to radiation treatment plans, this memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The radiation therapy treatment platform 200 also includes a radiation source 203 that operably couples and responds to the control circuit 201. So configured, the corresponding radiation beam 204 as emitted by the radiation source 203 can be selectively switched on and off by the control circuit 201. These teachings will also accommodate having the control circuit 201 control the relative strength of the radiation beam 204. Radiation sources are well understood in the art and require no further description here.

The radiation beam 204 is directed towards a multi-layer multi-leaf collimation system 205 that also operably couples to the control circuit 201 to thereby permit the control circuit 201 to control the movement of the collimation systems leaves and hence the formation and distribution of one or more beam-shaping and radiation-modulating apertures. The resultant modulated radiation beam 206 then reaches a treatment target in a corresponding patient 207.

Figure 3:
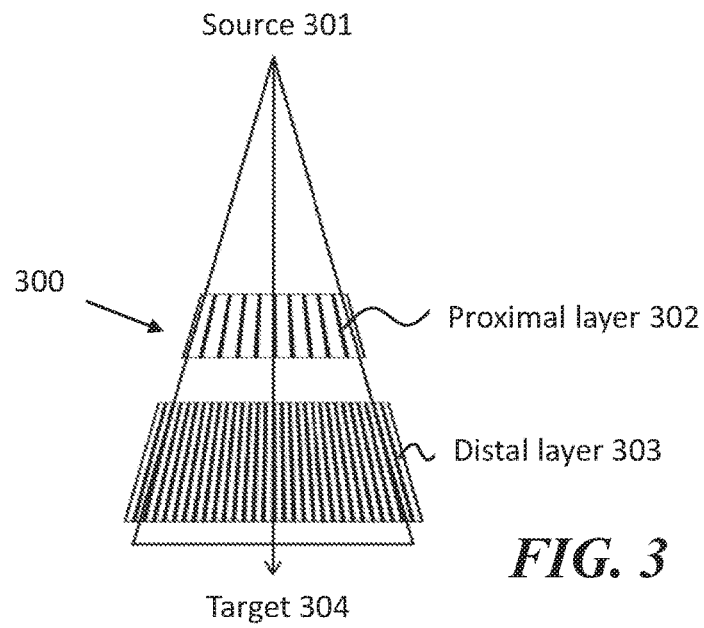
FIG. 3 comprises an illustration of a collimator system as configured in accordance with various embodiments of these teachings.

FIG. 3 presents a representative view a multi-layer multi-leaf collimator 300 of the multi-layer multi-leaf collimation system 205 according to some embodiments. The proximal layer 302 and distal layer 303 of the multi-layer multi-leaf collimator 300 are generally juxtaposed one atop the other with some amount of intervening space between the layers. In some embodiments, the intervening space between layers may range from 0.5 cm to a few centimeters. In some embodiments, the intervening space between layers is approximately 1 cm. The proximal layer 302 is oriented towards the radiation source 301 (and hence is relatively "proximal" to the radiation source 301) and the distal layer 303 is oriented opposite the radiation source 301 (with respect to the proximal layer 302) and towards the target 304 such as a patient. Generally speaking, this proximal layer 302 includes a plurality of selectively movable collimating leaf pairs each including a first leaf and a second leaf. So configured, when one or both collimating leaves of a pair of collimating leaves are selectively moved away from one another, a beam-shaping aperture forms therebetween. (The manner by which electric motors can be employed to effect such movement comprises a well-understood area of prior art endeavor. Accordingly, for the sake of brevity, additional details in those regards are not provided here.)

The distal layer 303 generally also includes pairs of collimating leaves, similar to the proximal layer 302. However, the proximal layer 302 and the distal layer 303 substantially differ in one or more of leaf transmission, penumbra width, maximum leaf speed, and median leaf width. For example, the distal layer 303 may comprise leaves with widths between 2 mm and 2 cm and the proximal layer 302 may comprise leaves with widths between 5 mm and 5 cm. In some embodiments, the median leaf width of the distal layer 303 may be 1.5-2.5 times larger than the median leaf width of the proximal layer 302. In some embodiments, the median leaf width of the proximal layer 302 may be 1.5-2.5 times larger than the median leaf width of the distal layer 303. Due to the difference in the dimensions between the multi-leaf collimator layers, the layers also differ in dosimetric properties and motion capabilities (e.g. maximum speed).

So configured, the distal layer 303 may be used, at least mainly, to produce conformal apertures that conform to the shape of the target volume with the primary purpose of blocking radiation entirely in certain areas. (As used herein to refer to the functionality and use of the multi-leaf collimator layers, terms such as "substantially" and "mainly" shall be understood to mean more than fifty percent of the corresponding functionality/usage of the respective layer. In some application settings it may be appropriate to require or specify larger percentages, such as at least sixty percent, seventy percent, eighty percent, ninety percent, or even one hundred percent.)

The proximal layer 302 may be used conversely, at least mainly, for in-field modulation (i.e., within the field of the target volume). The aperture of the proximal layer 302 may be optimized based on a target projection of the treatment area and the distal layer 303 may be optimized based on a fluence map describing the relative portions of radiation passing through different areas of the target projection. The fluence map may be later converted into a leaf sequence of the distal layer 303. In some embodiments, one of the layers may be controlled to create dose rate modulation together with the varying distal leaf positions.

Figure 4:
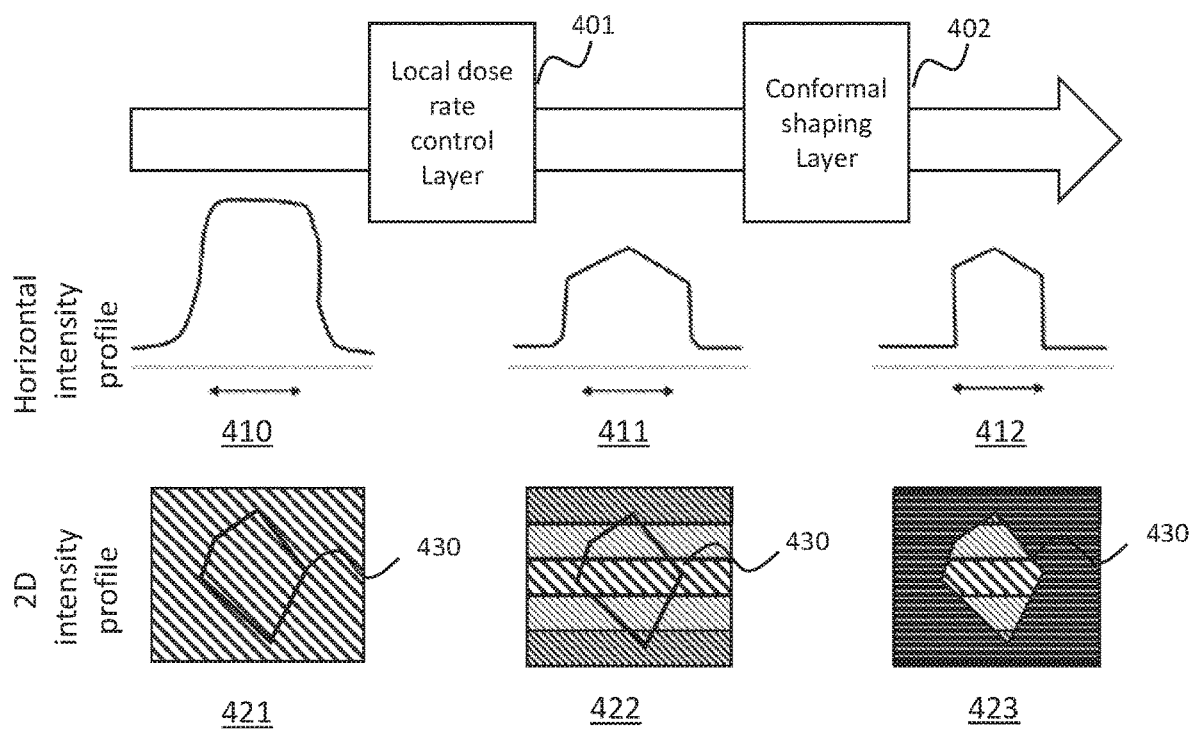
FIG. 4 comprises illustrations of intensity profiles in accordance with various embodiments of these teachings.

FIG. 4 presents an illustration of a radiation modulating process using a multi-layer multi-leaf collimator 300. Radiation intensity profiles of a radiation beam before and after the beam passes the local dose rate control layer 401 and the conformal shaping layer 402 are shown. In some embodiments, the local dose rate control layer 401 may comprise the proximal layer 302 and the conformal shaping layer 402 may comprise the distal layer 303, or vice versa.

The intensity profiles 410, 411, and 412 represent radiation intensities in the horizontal direction along one leaf. The arrows below the profile images correspond to the target range for treatment. The first profile 410 illustrates an unmodified beam from a radiation source. The second profile 411 illustrates the intensity profile of the radiation beam after the beam passesthrough the local dose rate control layer 401. At this stage, the profile height is modified, but the width of the radiation beam is not modified in the horizontal direction (direction of the leaves) and does not match the target range. The third profile 423 shows the radiation intensity profile after the beam has passed through both the local dose rate control layer 401 and the conformal shaping layer 402. The profile height is not further modified by the conformal shaping layer 402. The width of the resulting radiation intensity profile 412 now matches the target range.

In the 2D radiation intensity profiles 421, 422, and 423, lighter shadings corresponding to higher radiation intensity and darker shadings correspond to lower radiation intensity. The target projection 430 represents a treatment area according to a treatment plan. The leaves of the local dose rate control layer 401 and the conformal shaping layer 402 travel in the horizontal direction relative to the 2D intensity profiles shown in FIG. 4.

Intensity profile 421 represents the distribution of radiation intensity immediately after the source where radiation intensity is generally uniform in the field. Intensity profile 422 represents the distribution of radiation intensity after the beam passes through the local dose rate control layer 401. In profile 422, radiation intensity distribution is modified in stripes along the leaf direction. The number of stripes in the profile corresponds to the number of leaves in the local dose rate control layer 401. Intensity profile 423 represents the distribution of radiation intensity after the beam passes through the conformal shaping layer 402. In profile 423, the radiation intensity outside the target projection 430 is blocked by the shaping layer 402 and the intensity modulated stripes are visible within the target projection 430 region.

In some embodiments, the above optimization principle can be applied to different multi-leaf collimator designs. For example, the roles of distal and proximal layers can be switched and the division of roles can be different from above. In some embodiments, a multi-leaf collimator may have more than two layers and the treatment planning system may optimize each layer to primarily perform a different role such as dose rate control, beam modulation, and conformal shaping.

In some embodiments, the above approach is well suited for treatments where the beam direction relative to the patient is moving while the beam is on, such as in a conventional arc field system where the beam direction is changed by a rotating gantry. Typically, the degrees-of-freedom of aperture shaping varies more slowly than the degrees-of-freedom of field modulation. By these approaches, optimization efficiency is improved due to the amount of optimized degrees-of-freedoms (corresponding spatial variation of leaf positions and dose rate parameters) being split between two different optimization tasks.

FIG. 5 presents another representative view of a multi-layer multi-leaf collimator 500 for the multi-layer multi-leaf collimation system 205 according to some embodiments. The multi-layer multi-leaf collimator 500 includes a shaping layer 502 and a modulation layer 503 positioned between a source 501 and a patient 504. The shaping layer 502 is proximal to the source 501 while the modulation layer 503 is distal to the source 501.

Conventional radiation therapy treatment is based on delivering the same treatment plan multiple times. However, changes can occur between the capture of planning images and the administration of the treatment plan. The general approach is to take this uncertainty in treatment-time patient anatomy into account by adding margins to the delineated structures at planning time. Images taken just prior to the treatment can also be used for on-line adaptation of the plan.

The multi-layer multi-leaf collimator 500 may be used for adaptive treatment delivery by using the modulation layer 503 to modulate the beam intensity profile to a region somewhat larger than the expected target projection and using the conformal shaping layer 502 to restrict the aperture to the target projection at the time of the treatment. By this approach, the adaptation of the treatment plan may only include the reshaping of the aperture in the second layer. A 3D image reconstruction may be eliminated since target projection may be determined from the directions of the fields alone. As such, plans generated using the proposed approach can be adapted quickly, using only 2D images if necessary. These approaches also reduce the requirements for quality assurance since the dynamic part of the sequence (e.g. the motion of the shaping layer 502) is not changed at treatment time. The technique is also an improvement from simple isocenter shift since it can provide more uniform dose distribution and the plan can be adapted to various target shape changes and not only translations. While the modulation layer 503 is shown as the distal layer in FIG. 5, in some embodiments, the dynamic modulation layer 503 could either be the layer closer to the source of radiation (hence the proximal layer) or the layer closer to the patient (hence the distal layer).

FIGS. 6A and 6B represent beam-eye views of an intensity-modulated radiation therapy (IMRT) field. FIG. 6A represents a treatment plan created based on a target projection 601, which may be based on planning images captured prior to the treatment. A target projection region with adaptation margin 602 is determined based on the planning image of the target projection 601. A region of dynamic modulation 603 is then determined to encompass the target projection with adaptation margin 602. FIG. 6B represents the adaptations at the time of the treatment. In FIG. 6B, the actual target projection 601' deviates from the planning image of the target projection 601. To adapt to this change, the shaping aperture 611 is adjusted based on the actual target projection 601'. In some embodiments, the shaping layer 502 of the collimator is controlled to define the region of dynamic modulation 603 during treatment, while the modulation layer 503 is controlled to create the adapted shaping aperture 611 in response to changes of the target projection 601'. The system may further monitor the adapted shaping aperture 611 to ensure that it remains within the region of dynamic modulation 603 during treatment.

By this approach, the leaf sequence for the IMRT field uses the dynamic layer leaf motion to yield a uniform dose distribution for a target volume with an extended 3D margin as shown in FIGS. 6A and 6B. The size of the margin region may be determined based on the expected movement of the target. During the planning process, the shaping layer aperture can be set to follow the extended region of dynamic modulation 603 to define the area where the adaptation may be done. Quality assurance may be performed to verify that the machine is able to reproduce the dynamic leaf pattern with sufficient dosimetric accuracy.

At the time of treatment, when the actual target projection is determined, the aperture of the shaping layer is reduced to the recognized treatment time aperture. The shaping aperture adaptation may be carried out while the gantry is moving into position. In some instances, adaptation may be needed on only one side of the target, such as the side proximal to a critical organ. Additionally, adaptation may be performed based on 2D images (such as kV images) from the direction of the field without reconstructing a 3D CT image.

In some embodiments, a treatment plan may be created using the actual target with the aforementioned extended 3D margin if the delivery method described above is created using inverse planning optimization. When optimization is done this way, the dose in critical organs is biased to be larger than the value actually delivered since the adaptive action reduces the shaping aperture and decreases the total dose delivered. The bias may be reduced by taking into account that the expected dose accumulation in the target extension volume decreases with distance from the surface of the non-extended target. For example, critical organ dosage can be determined based on an expected dose distribution calculated by reducing the fluence value in the extended aperture region. By some approaches, the adaptive treatment can provide more robust results if dose robustness is further taken into account in the optimization time by adding a bias to the optimization to prefer smooth leaf sequences in the dynamic layer. The plan can further be optimized to use beam directions that are also good imaging directions.

In some embodiments, various methods and apparatuses described herein may also be applied to Volumetric Arc Therapy (VMAT) fields. In VMAT fields, both collimator layers would be dynamic but the shaping layer leaves would have a slower motion and be configured to follow the target projection.

With continued reference to the foregoing illustrations, and in particular to FIGS. 1 and 2, process 100 provides radiation modulation in radiation therapy. As is well understood in the art, generating a radiation treatment plan typically relies upon models for one or more aspects of the radiation therapy treatment platform. It is also well understood that generating a radiation treatment plan often entails making use of iterative optimization processes. As used herein, "optimization" will be understood to refer to improving a treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects. Since optimization practices themselves are a well-understood area of prior art endeavor, further details are not provided herein these regards for the sake of brevity and simplicity.

By some approaches, the steps of FIG. 1 are performed with a multi-layer multi-leaf collimation system of a radiation therapy treatment platform. In some embodiments, the multi-layer multi-leaf collimation system may comprise one or more of the multi-layer multi-leaf collimation system 205, the multi-layer multi-leaf collimator 300, and/or the multi-layer multi-leaf collimator 500. By some approaches, the multi-layer multi-leaf collimation system comprises a first multi-leaf collimator layer and a second multi-leaf collimator layer. The first multi-leaf collimator layer may substantially differ from the second multi-leaf collimator layer in one or more of leaf transmission, penumbra width, maximum leaf speed, and median leaf width. In some embodiments, the median width of the second set of leaves is substantially larger than a median width of the first set of leaves. In some embodiments, the first multi-leaf collimator layer is configured to primarily perform a first function to affect a radiation beam traveling from a radiation source to a target and the second multi-leaf collimator layer is configured to primarily perform a second function, different from the first function, to affect the radiation beam.

In step 101, the control circuit retrieves a treatment plan for the multi-layer multi-leaf collimation system. In some embodiments, the treatment plan uses each layer to primarily perform a different role such as dose rate control, beam modulation, and conformal shaping. In some embodiments, the treatment plan uses one layer of the multi-leaf collimator to define a treatment area based on a planning image and an adaptation margin and uses a second layer for adaptation. In some embodiments, motions of each layer are optimized for the treatment plan based on their individual maximum speed capability.

In step 102, the control circuit controls the first multi-leaf collimator layer that comprises a part of a discrete multi-leaf collimator to primarily perform a first function to affect a radiation beam traveling from a radiation source to a target. In some embodiments, the first function comprises shaping the radiation beam by forming a first aperture according to a profile of a target area of a treatment plan to block out radiation outside of the target area. The aperture may correspond to a planning image with an adaptation margin.

In step 103, the control circuit controls a second multi-leaf collimator layer that also comprises an integral part of the discrete multi-leaf collimator to primarily perform a second function, different from the first function, to affect the radiation beam. In some embodiments, the second function comprises modulating a fluence distribution of the radiation beam by modulating a second aperture to vary radiation intensities in different regions within a target area according to a treatment plan. In some embodiments, the second function comprises adaptively shaping the aperture to the target projection at the time of the treatment.

By some approaches, steps 102 and 103 may be carried out simultaneously or in close succession to coordinate the movements of the multi-leaf collimator layers and other components of the system. Steps 102 and 103 may be performed repeatedly during a treatment session from different angles to carry out a treatment plan.

It shall be understood that the foregoing process 100 is quite flexible in practice and can be modified to accommodate variations, modifications, or even substitutions as regards the foregoing details. By some approaches, the first multi-leaf collimator layer may comprise a distal layer 303 and the second multi-leaf collimator layer may comprise a proximal layer 302, or vice versa. By some approaches, the first multi-leaf collimator layer may comprise the shaping layer 502 and the second multi-leaf collimator layer may comprise the modulation layer 503, or vice versa. By some approaches, the first multi-leaf collimator layer may have a larger leaf transmission, penumbra width, maximum leaf speed, and/or median leaf width as compared to the second multi-leaf collimator layer, or vice versa.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method for radiation modulation in radiation therapy comprising:

providing a first multi-leaf collimator layer that is disposed proximal to a radiation source and that comprises a part of a discrete multi-leaf collimator, the first multi-leaf collimator layer being configured to primarily perform a first function as regards affecting a radiation beam traveling from the radiation source to a target and wherein leaves of the first multi-leaf collimator layer are constrained to a first maximum speed;

providing a second multi-leaf collimator layer that is positioned distal to the radiation source and that also comprises an integral part of the discrete multi-leaf collimator, the second multi-leaf collimator level being configured to primarily perform a second function as regards affecting the radiation beam that is different from the first function, and wherein leaves of the second multi-leaf collimator layer are constrained to a second maximum speed that is higher than the first maximum speed; and optimizing a radiation treatment plan that utilizes both of the first and second multi-leaf collimator layers wherein the leaves in each of the first and second multi-leaf collimator layers are optimized according to each layer's specific maximum speed constraint for layer-specific functions, such that motions of each layer are optimized for the radiation treatment plan based on their individual maximum speed capability.

2. The method of claim 1 wherein the first function comprises shaping the radiation beam to conform to a target area.

3. The method of claim 1 wherein controlling the first multi-leaf collimator layer comprises forming a first aperture according to a profile of a target area of a treatment plan to block out radiation outside of the target area.

4. The method of claim 1 wherein the second function comprises modulating a fluence distribution of the radiation beam.

5. The method of claim 1 wherein controlling the second multi-leaf collimator layer comprises modulating a second aperture to vary radiation intensities in different regions within a target area according to a treatment plan.

6. The method of claim 1 wherein the first multi-leaf collimator layer further substantially differs from the second multi-leaf collimator layer in one or more of leaf transmission, penumbra width, and median leaf width.

\* \* \* \* \*